US012236585B2

(12) United States Patent
Kim et al.

(10) Patent No.: US 12,236,585 B2
(45) Date of Patent: Feb. 25, 2025

(54) METHOD FOR MEASURING LESION OF MEDICAL IMAGE

(71) Applicant: VUNO Inc., Seoul (KR)

(72) Inventors: Yeong Won Kim, Seoul (KR); Kyungdoc Kim, Seoul (KR); Hong Seok Lee, Seoul (KR); Hyeongsub Kim, Seoul (KR)

(73) Assignee: VUNO Inc., Seoul (KR)

( * ) Notice: Subject to any disclaimer, the term of this patent is extended or adjusted under 35 U.S.C. 154(b) by 380 days.

(21) Appl. No.: 17/582,717

(22) Filed: Jan. 24, 2022

(65) Prior Publication Data

US 2022/0237777 A1  Jul. 28, 2022

(30) Foreign Application Priority Data

Jan. 26, 2021  (KR) .................. 10-2021-0011021
Jan. 11, 2022  (KR) .................. 10-2022-0003788

(51) Int. Cl.
*G06T 7/00*  (2017.01)
*G06V 10/40*  (2022.01)
(Continued)

(52) U.S. Cl.
CPC ............ *G06T 7/0012* (2013.01); *G06V 10/40* (2022.01); *G06V 10/774* (2022.01); *G06V 10/776* (2022.01); *G06V 10/82* (2022.01); *G16H 30/40* (2018.01); *G16H 50/20* (2018.01); *A61B 6/5217* (2013.01); *G06T 2207/20076* (2013.01); *G06T 2207/20081* (2013.01); *G06T 2207/20084* (2013.01); *G06T 2207/30081* (2013.01); *G06T 2207/30096* (2013.01); *G06V 2201/03* (2022.01)

(58) Field of Classification Search
CPC ..................... G06T 7/0012; G06T 7/00; G06T 2207/30081; G06T 2207/30096; G06T 2207/20081; G06T 2207/20084; G06T 2207/20076; G16H 50/20; G16H 30/40; A61B 6/5217; G06V 10/82; G06V 10/774; G06V 10/776
See application file for complete search history.

(56) References Cited

U.S. PATENT DOCUMENTS 8,139,831 B2   3/2012 Khamene et al.
10,192,099 B2  1/2019 Agaian et al.
(Continued)

FOREIGN PATENT DOCUMENTS

KR    10-2018-0066983 A   6/2018
KR       10-1889722 B1    8/2018
(Continued)

*Primary Examiner* — Tuan H Nguyen
(74) *Attorney, Agent, or Firm* — Seed IP Law Group LLP

(57) ABSTRACT

According to the embodiment of the present disclosure, a method of analyzing a lesion based on a medical image performed by a computing device is disclosed. The method may include: extracting, by using a pre-trained artificial neural network, a first feature for each tile of a plurality of tiles included in an input image; and extracting, by using the pre-trained artificial neural network, a second feature for an entirety of the input image, based on information about whether the lesion is present for the each tile and information on a pattern of the lesion for the each tile generated based on first features of the plurality of tiles.

12 Claims, 10 Drawing Sheets

(51) Int. Cl.
*G06V 10/774* (2022.01)
*G06V 10/776* (2022.01)
*G06V 10/82* (2022.01)
*G16H 30/40* (2018.01)
*G16H 50/20* (2018.01)
*A61B 6/00* (2006.01)

(56) References Cited

U.S. PATENT DOCUMENTS

| 11,074,686 B2* | 7/2021 | Kim ..................... G06F 17/15 |
| 2020/0043164 A1* | 2/2020 | Fuchs ................ G06F 18/2323 |
| 2020/0293748 A1 | 9/2020 | Avenel et al. |
| 2021/0304889 A1 | 9/2021 | Lee et al. |
| 2021/0391076 A1 | 12/2021 | Kwak et al. |

FOREIGN PATENT DOCUMENTS

| KR | 10-2019-0143510 A | 12/2019 |
| KR | 10-2020-0000541 A | 1/2020 |
| KR | 10-2020-0044183 A | 4/2020 |

* cited by examiner

METHOD FOR MEASURING LESION OF MEDICAL IMAGE

CROSS-REFERENCE TO RELATED APPLICATIONS

This application claims priority to and the benefit of Korean Patent Application No. 10-2021-0011021 filed in the Korean Intellectual Property Office on Jan. 26, 2021 and Korean Patent Application No. 10-2022-0003788 filed in the Korean Intellectual Property Office on Jan. 11, 2022, the entire contents of which are incorporated herein by reference.

BACKGROUND

Technical Field

The present disclosure relates to a method of processing a medical image, and more particularly, to a method of detecting and evaluating a lesion of a body tissue existing in a medical image by using an artificial neural network.

Description of the Related Art

Medical images are data that enable people to understand physical states of various tissues of the human body. The medical image includes a digital radiographic image (X-ray), a Computed Tomography (CT) image, a Magnetic Resonance Imaging (MRI) image, a pathology slide image, and the like.

As digital pathology has recently begun to draw attention in the medical field, various technologies have been developed for acquiring, processing, and analyzing pathology slide images among medical images. For example, one of the representative prior art relates to a method of identifying the distribution of lesions (for example, prostate cancer) present in a pathology slide image using a deep learning algorithm and evaluating the entire tissue.

US Patent Application Publication No. 2020-0293748 (Sep. 17, 2020) discloses a method of classifying prostate cancer.

BRIEF SUMMARY

The inventors of the present disclosure have recognized and appreciated that although the prior art can reduce the time and cost required for diagnosing a lesion, there is a disadvantage in that it cannot provide evaluation results for the lesion for each tissue area. Therefore, the prior art has a problem in that it cannot effectively provide quantitative or qualitative information necessary for diagnosis of lesions. Further, according to some approaches in the prior art, there is a disadvantage in that it is not easy to obtain data for building a deep learning model because the type and number of data that can be used for learning are inevitably limited in order to analyze the tissue by area due to the structure of the deep learning model.

The present disclosure has been conceived in response to one or more problems in the related art including the above-noted problems, and has been made in an effort to provide a method of identifying and evaluating a lesion of a tissue present in a medical image for pathological diagnosis.

An embodiment of the present disclosure discloses a method of analyzing a lesion based on a medical image performed by a computing device. The method may include: extracting a first feature of each of a plurality of tiles included in an input image by using a pre-trained artificial neural network; analyzing whether a lesion is present for each tile based on the first feature for each of the plurality of tiles by using the pre-trained artificial neural network; analyzing a pattern of the lesion for each tile based on the first feature for each of the plurality of tiles by using the pre-trained artificial neural network; and extracting a second feature for the entire input image based on the analyzing of whether the lesion is present for each tile and the analyzing of the pattern of the lesion for each tile by using the pre-trained artificial neural network.

In an alternative embodiment, the input image may be an image including a prostate tissue, and the pattern of the lesion may correspond to the Gleason pattern, and the method may further include determining a prostate cancer score for the entire input image based on the second feature by using the pre-trained artificial neural network.

In the alternative embodiment, the extracting of the second feature for the entire input image may include: sampling some of the plurality of tiles; and extracting the second feature based on analysis data representing whether the lesion is present for the sampled tiles and analysis data representing the pattern of the lesion for the sampled tiles by using the pre-trained artificial neural network.

In the alternative embodiment, the analyzing of whether the lesion is present for each tile and the analyzing of the pattern of the lesion for each tile may be performed in an encoder part of the pre-trained artificial neural network, and the extracting of the second feature for the entire input image may be performed in a decoder part of the pre-trained artificial neural network.

In the alternative embodiment, the method may further include: generating a map representing the pattern of the lesion included in the input image as a first output based on the information about the pattern of the lesion for each tile; determining an evaluation score of the lesion for the entire input image based on the second feature by using the pre-trained artificial neural network; and generating the determined evaluation score as a second output.

In the alternative embodiment, the method may further include determining an evaluation score of the lesion for the input image based on the second feature by using the pre-trained artificial neural network, and the pre-trained artificial neural network may include a main model trained based on a comparison between an evaluation score determined for a predetermined image and a score labeled to the predetermined image.

In the alternative embodiment, the pre-trained artificial neural network may include the main model additionally trained based on a comparison between an average of first probability values representing whether the lesion is present in the plurality of tiles included in the predetermined image and a probability value labeled to the predetermined image without labeling of a tile level.

In the alternative embodiment, the analyzing of whether the lesion is present for each tile may include: determining a first probability value representing whether the lesion is present for each tile of the plurality of tiles by using a main model of the pre-trained artificial neural network; determining a second probability value representing whether the lesion is present for each tile of the plurality of tiles by using a sub model of the pre-trained artificial neural network; and correcting the first probability value based on the second probability value, and the sub model may be trained based on labeling of the tile level.

In the alternative embodiment, the pre-trained artificial neural network may include the main model additionally trained by comparing patterns of the lesion of the tiles satisfying a predetermined reference between the images having corresponding patterns of the lesion at an image level without labeling of the tile level.

In the alternative embodiment, the analyzing of the pattern of the lesion for each tile may include: determining a probability value representing whether the lesion is present for each tile of the plurality of tiles by using a sub model of the pre-trained artificial neural network; and correcting the pattern of the lesion for each tile based on the probability value, and the sub model may be trained based on labeling of the tile level.

Another embodiment of the present disclosure discloses a computer program stored in a computer readable storage medium. The computer program may cause a processor to perform operations for analyzing a medical image, the operations including: an operation of extracting a first feature of each of a plurality of tiles included in an input image by using a pre-trained artificial neural network; an operation analyzing whether a lesion is present for each tile based on the first feature for each of the plurality of tiles by using the pre-trained artificial neural network; an operation of analyzing a pattern of the lesion for each tile based on the first feature for each of the plurality of tiles by using the pre-trained artificial neural network; and an operation of extracting a second feature for the entire input image based on the analyzing of whether the lesion is present for each tile and the analyzing of the pattern of the lesion for each tile by using the pre-trained artificial neural network.

Another embodiment of the present disclosure discloses a computing device for analyzing a lesion based on a medical image. The device may include: at least one processor; and a memory coupled to at least one processor, and one or more processors may be configured to extract a first feature of each of a plurality of tiles included in an input image by using a pre-trained artificial neural network; analyze whether a lesion is present for each tile based on the first feature for each of the plurality of tiles by using the pre-trained artificial neural network; analyze a pattern of the lesion for each tile based on the first feature for each of the plurality of tiles by using the pre-trained artificial neural network; and extract a second feature for the entire input image based on the analyzing of whether the lesion is present for each tile and the analyzing of the pattern of the lesion for each tile by using the pre-trained artificial neural network.

Another embodiment of the present disclosure discloses a method of analyzing a lesion based on a medical image performed by a computing device. The method may include: extracting a first feature of each of a plurality of tiles included in an input image by using a pre-trained artificial neural network; analyzing a pattern of a lesion for each tile based on the first feature for each of the plurality of tiles by using the pre-trained artificial neural network; and providing a map representing a pattern of the lesion included in the input image based on the analyzing of the pattern of the lesion for each tile, and the analyzing of the pattern of the lesion for each tile may be performed by a model trained without labeling of a tile level.

In an alternative embodiment, the method may further include: analyzing a probability of presence of the lesion of each of the plurality of tiles included in the input image by using a sub model; and correcting a result of the analysis of the pattern of the lesion for each tile based on the analyzing of the probability of the presence of the lesion of each of the plurality of tiles, and the sub model may be trained based on labeling of a tile level.

In the alternative embodiment, the model trained without the labeling of the tile level may be trained by comparing patterns of the tiles satisfying a predetermined reference between images having corresponding patterns of the lesion at an image level.

The present disclosure may provide a method of identifying and evaluating a lesion of a tissue present in a medical image for pathological diagnosis.

DETAILED DESCRIPTION

Figure 1:
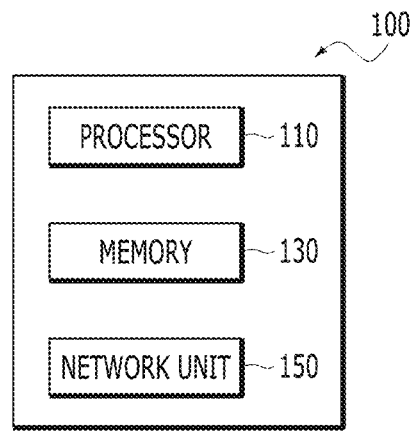
FIG. 1 is a block diagram of a computing device for evaluating a lesion present in a medical image according to an embodiment of the present disclosure.

Hereinafter, various embodiments are described with reference to the drawings. In the present specification, various descriptions are presented for understanding the present disclosure. However, it is obvious that the embodiments may be carried out even without a particular description.

Terms, "component," "module," "system," and the like used in the present specification indicate a computer-related entity, hardware, firmware, software, a combination of software and hardware, or execution of software. For example, a component may be a procedure executed in a processor, a processor, an object, an execution thread, a program, and/or a computer, but is not limited thereto. For example, both an application executed in a computing device and the computing device may be components. One or more components may reside within a processor and/or an execution thread. One component may be localized within one computer. One component may be distributed between two or more computers. Further, the components may be executed by various computer readable medium having various data structures stored therein. For example, components may communicate through local and/or remote processing according to a signal (for example, data transmitted to another system through a network, such as Internet, through data and/or a signal from one component interacting with another component in a local system and a distributed system) having one or more data packets.

A term "or" intends to mean comprehensive "or," not exclusive "or." That is, unless otherwise specified or when it is unclear in context, "X uses A or B" intends to mean one of the natural comprehensive substitutions. That is, when X uses A, X uses B, or X uses both A and B, "X uses A or B" may be applied to any one among the cases. Further, a term "and/or" used in the present specification shall be understood to designate and include all of the possible combinations of one or more items among the listed relevant items.

A term "include" and/or "including" shall be understood as meaning that a corresponding characteristic and/or a constituent element exists. Further, a term "include" and/or "including" means that a corresponding characteristic and/or a constituent element exists, but it shall be understood that the existence or an addition of one or more other characteristics, constituent elements, and/or a group thereof is not excluded. Further, unless otherwise specified or when it is unclear that a single form is indicated in context, the singular shall be construed to generally mean "one or more" in the present specification and the claims.

The term "at least one of A and B" should be interpreted to mean "the case including only A," "the case including only B," and "the case where A and B are combined."

Those skilled in the art shall recognize that the various illustrative logical blocks, configurations, modules, circuits, means, logic, and algorithm operations described in relation to the embodiments additionally disclosed herein may be implemented by electronic hardware, computer software, or in a combination of electronic hardware and computer software. In order to clearly exemplify interchangeability of hardware and software, the various illustrative components, blocks, configurations, means, logic, modules, circuits, and operations have been generally described above in the functional aspects thereof. Whether the functionality is implemented as hardware or software depends on a specific application or design restraints given to the general system. Those skilled in the art may implement the functionality described by various methods for each of the specific applications. However, it shall not be construed that the determinations of the implementation deviate from the range of the contents of the present disclosure.

The description about the presented embodiments is provided so as for those skilled in the art to use or carry out the present disclosure. Various modifications of the embodiments will be apparent to those skilled in the art. General principles defined herein may be applied to other embodiments without departing from the scope of the present disclosure. Therefore, the present disclosure is not limited to the embodiments presented herein. The present disclosure shall be interpreted within the broadest meaning range consistent to the principles and new characteristics presented herein.

In the present specification, a neural network, an artificial neural network, and a network function may often be interchangeably used.

Meanwhile, the term "image" or "image data" used throughout the detailed description and claims of the present disclosure refers to multi-dimensional data constituted by discrete image elements (e.g., pixels in a 2D image), and in other words, refers to an object which may be seen with an eye (e.g., displayed on a video screen) or a digital representation of the object (such as a file corresponding to a pixel output of CT, MRI detector, etc.).

For example, the "image" may be computed tomography (CT), magnetic resonance imaging (MRI), ultrasonic waves, a medical image of a subject collected by any other medical imaging system known in the technical field of the present disclosure. The image may not particularly be provided in a medical context, and may be provided in a non-medical context, and may be for example, a security search X-ray imaging.

Throughout the detailed description and claims of the present disclosure, a 'Digital Imaging and Communications in Medicine (DICOM)' standard is a term which collectively refers to several standards used for digital image representation and communication in a medical device, so that the DICOM standard is announced by the Federation Committee, constituted in the American College Radiology (ACR) and the National Electrical Manufacturers Association (NEMA).

Throughout the detailed description and claims of the present disclosure, a 'Picture Archiving and Communication System (PACS)' is a term that refers to a system for performing storing, processing, and transmitting according to the DICOM standard, and medical images obtained by using digital medical image equipment such as X-ray, CT, and MRI may be stored in a DICOM format and transmitted to terminals inside or outside a hospital through a network, and additionally include a reading result and a medical chart.

FIG. 1 is a block diagram of a computing device for evaluating a lesion based on a medical image according to an embodiment of the present disclosure.

FIG. 1 is a block diagram of a computing device for detecting a serial section of a medical image according to an embodiment of the present disclosure.

A configuration of the computing device 100 illustrated in FIG. 1 is only an example shown through simplification. In an embodiment of the present disclosure, the computing device 100 may include other components for performing a computing environment of the computing device 100 and only some of the disclosed components may constitute the computing device 100.

The computing device 100 may include a processor 110, a memory 130, and a network unit 150.

The processor 110 may be constituted by one or more cores and may include processors for data analysis and deep learning, which include a central processing unit (CPU), a general purpose graphics processing unit (GPGPU), a tensor processing unit (TPU), and the like of the computing device. The processor 110 may read a computer program stored in the memory 130 to perform data processing for machine learning according to an embodiment of the present disclosure. According to an embodiment of the present disclosure, the processor 110 may perform a calculation for learning the neural network. The processor 110 may perform calculations for learning the neural network, which include processing of input data for learning in deep learning (DL), extracting a feature in the input data, calculating an error, updating a weight of the neural network using backpropagation, and the like. At least one of the CPU, GPGPU, and TPU of the processor 110 may process learning of a network function. For example, both the CPU and the GPGPU may process the learning of the network function and data classification using the network function. Further, in an embodiment of the present disclosure, processors of a plurality of computing devices may be used together to process the learning of the network function and the data classification using the network function. Further, the computer program executed in the computing device according to an embodiment of the present disclosure may be a CPU, GPGPU, or TPU executable program.

The processor 110 according to the embodiment of the present disclosure may perform an evaluation and an analysis for each area of a tissue present in a medical image. In this case, the medical image may be a pathology slide image including a tissue, such as a prostate. For example, the processor 110 may extract features by distinguishing the pathology slide image for each tile by using a pre-trained first deep learning model. In this case, the tile may also be a pixel that is a basic configuration unit of the image, or a set of pixels.

The processor 110 may predict a pattern of a lesion (for example, a Gleason pattern) of each tile based on a feature of each tile by using a pre-trained second deep learning model. Further, the processor 110 may output a map (for example, a heat map) representing a pattern of a lesion (for example, a pattern of prostate disease) based on a result of the prediction for each tile. Meanwhile, the second deep learning model may be trained by a weakly supervised learning method. For example, the second deep learning model may be trained without tile-level labeling by calculating a loss function for tiles that satisfy a predetermined reference (for example, the tumor probability exceeds a preset threshold value) between medical images having corresponding Gleason patterns at an image level (for example, between medical images having corresponding major and minor Gleason patterns).

The processor 110 may also predict whether a lesion is present (for example, whether a tumor of the prostate tissue is present) in each tile based on a feature for each tile by using a pre-trained third deep learning model. In this case, the processor 110 may output, for example, a probability value representing analysis information regarding the presence or absence of the tumor for each tile. Herein, the probability value may be a binary classification value or a particular numerical value. Meanwhile, the third deep learning model may also be trained by a weakly supervised learning method. For example, the third deep learning model may be trained based on a loss function by comparing an average of probability values representing whether the lesion is present for the plurality of tiles included in a predetermined medical image with a probability value labeled to the predetermined medical image (a probability value labeled at an image level) without tile-level labeling.

The processor 110 may perform an evaluation for the entire tissues present in the medical image. For example, the processor 110 may integrate the feature for each tile for the pattern of the lesion (for example, the Gleason pattern) and the feature for each tile regarding the presence and absence of the lesion (for example, the presence and absence of the tumor of the prostate tissue) by using a pre-trained fourth deep learning model. That is, the processor 110 may extract the features of the entire pathology slide image by combining the feature for each tile including the result of the prediction of the pattern of the lesion and the feature for each tile including the result of the prediction for the presence or absence of the lesion through the fourth deep learning model. Further, the processor 110 may also perform an evaluation for the entire tissue based on features for sampled tiles. For example, the processor 110 may sample (for example, randomly sample) N tiles among the whole tiles of the medical image, integrate a feature for each tile for a pattern of a lesion and a feature for each tile for the presence or absence of the lesion only for the N sampled tiles, and extract the feature for the entire medical image based on the integrated features.

The processor 110 may predict an evaluation score (for example, the Gleason grade of the prostate) of the lesion present in the pathology slide image based on the features of the entire image generated by combining the feature for each tile by using a pre-trained fifth deep learning model. Meanwhile, the fourth deep learning model and the fifth deep learning model may be trained by a supervised learning method. For example, the fourth deep learning model and the fifth deep learning model may be trained based on the comparison between the Gleason grade analyzed for the entire medical image and the grade labeled for the medical image (labeled at the image level).

The processor 110 may analyze a pattern of the lesion of each tile and analyze whether the lesion is present in each tile by utilizing an encoder of a pre-trained artificial neural network. For example, the second deep learning model and the third deep learning model may be included in the encoder part of the pre-trained artificial neural network. Further, the processor may perform an evaluation for the entire tissues present in the medical image by utilizing a decoder part of the pre-trained artificial neural network. For example, the fourth deep learning model and the fifth deep learning model may be included in the decoder part of the pre-trained artificial neural network.

The processor 110 may correct data analyzed in the second deep learning model, the third deep learning model, and the fifth deep learning model by additionally utilizing a sub deep learning model, thereby improving accuracy of the prediction. For example, the processor 110 may correct the data obtained by analyzing the pattern of the lesion of each tile and the data obtained by analyzing whether the lesion is present in each tile by additionally utilizing the sub deep learning model, and resultantly, the result of the analysis for the entire medical image may be improved. Meanwhile, the sub deep learning model may output an additional probability value regarding the presence or absence of the lesion for each of the tiles included in the medical image. For example, the sub deep learning model may output a probability value of a particular numerical value or binary classification values of benign/malignant. In addition, the sub deep learning model may be trained by a supervised learning method utilizing a label, and through this, it is possible to give the effect of the additional performance improvement even to the case where the second deep learning model or the third deep learning model is not trained by the supervised training method (for example, when the second deep learning model or the third deep learning model is trained by the weakly supervised learning and the like).

According to an embodiment of the present disclosure, the memory 130 may store any type of information generated or determined by the processor 110 and any type of information received by the network unit 150.

According to an embodiment of the present disclosure, the memory 130 may include at least one type of storage medium of a flash memory type storage medium, a hard disk type storage medium, a multimedia card micro type storage medium, a card type memory (for example, an SD or XD memory, or the like), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk. The computing device 100 may operate in connection with a web storage performing a storing function of the memory 130 on the Internet. The description of the memory is just an example and the present disclosure is not limited thereto.

The network unit 150 according to an embodiment of the present disclosure may use an arbitrary type wired/wireless communication systems.

The network unit 150 may receive a medical image representing a physical tissue from a medical image storage and transmission system. For example, the medical image representing the physical tissue may be learning data or inference data of the neural network model. The medical image representing the physical tissue may be a pathology slide image including at least one tissue. In this case, the pathology slide image may be appreciated as a scan image obtained from the glass slide through a scanner and stored in the medical image storage and transmission system for pathology diagnosis. The medical image representing the physical tissue is not limited to the above-described example, but may include all images related to the physical tissue acquired through photographing, such as an X-ray image, a CT image, etc.

The network unit 150 may transmit and receive information processed by the processor 110, a user interface, etc., through communication with the other terminal. For example, the network unit 150 may provide the user interface generated by the processor 110 to a client (e.g., a user terminal). Further, the network unit 150 may receive an external input of a user applied to the client and deliver the received external input to the processor 110. In this case, the processor 110 may process operations such as output, modification, change, addition, etc., of information provided through the user interface based on the external input of the user delivered from the network unit 150.

Meanwhile, according to an embodiment of the present disclosure, the computing device 100 as a computing system that transmits and receives information to and from the client through communication may include a server. In this case, the client may be any type of terminal which may access the server. For example, the computing device 100 which is the server may receive the medical image from the medical image photographing system and analyze the lesion, and provide a user interface including an analysis result to the user terminal. In this case, the user terminal may output the user interface received from the computing device 100 as the server, and receive and process the information through an interaction with the user.

In an additional embodiment, the computing device 100 may also include any type of terminal that performs additional information processing by receiving a data resource generated in any server.

Figure 2:
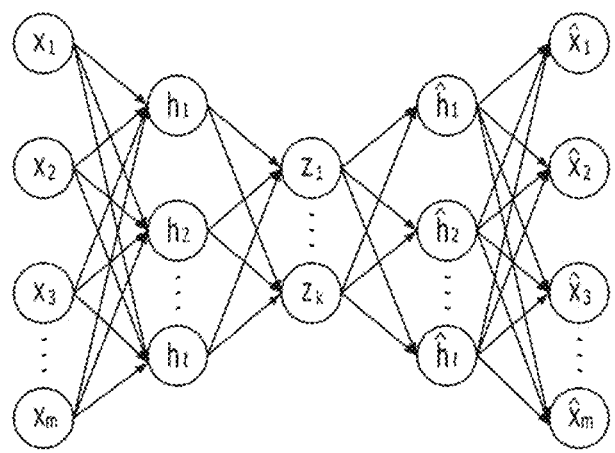
FIG. 2 is a schematic diagram illustrating a network function according to an embodiment of the present disclosure.

FIG. 2 is a schematic diagram illustrating a network function according to an embodiment of the present disclosure.

Throughout the present disclosure, a deep learning model, the neural network, a network function, and the neural network may be used as an interchangeable meaning. The neural network may be generally constituted by an aggregate of calculation units which are mutually connected to each other, which may be called nodes. The nodes may also be called neurons. The neural network is configured to include one or more nodes. The nodes (alternatively, neurons) constituting the neural networks may be connected to each other by one or more links.

In the neural network, one or more nodes connected through the link may relatively form the relationship between an input node and an output node. Concepts of the input node and the output node are relative and a predetermined node which has the output node relationship with respect to one node may have the input node relationship in the relationship with another node and vice versa. As described above, the relationship of the input node to the output node may be generated based on the link. One or more output nodes may be connected to one input node through the link and vice versa.

In the relationship of the input node and the output node connected through one link, a value of data of the output node may be determined based on data input in the input node. Here, a link connecting the input node and the output node to each other may have a weight. The weight may be variable and the weight is variable by a user or an algorithm in order for the neural network to perform a desired function. For example, when one or more input nodes are mutually connected to one output node by the respective links, the output node may determine an output node value based on values input in the input nodes connected with the output node and the weights set in the links corresponding to the respective input nodes.

As described above, in the neural network, one or more nodes are connected to each other through one or more links to form a relationship of the input node and output node in the neural network. A characteristic of the neural network may be determined according to the number of nodes, the number of links, correlations between the nodes and the links, and values of the weights granted to the respective links in the neural network. For example, when the same number of nodes and links exist and there are two neural networks in which the weight values of the links are different from each other, it may be recognized that two neural networks are different from each other.

The neural network may be constituted by a set of one or more nodes. A subset of the nodes constituting the neural network may constitute a layer. Some of the nodes constituting the neural network may constitute one layer based on the distances from the initial input node. For example, a set of nodes of which distance from the initial input node is n may constitute n layers. The distance from the initial input node may be defined by the minimum number of links which should be passed through for reaching the corresponding node from the initial input node. However, definition of the layer is predetermined for description and the order of the layer in the neural network may be defined by a method different from the aforementioned method. For example, the layers of the nodes may be defined by the distance from a final output node.

The initial input node may mean one or more nodes in which data is directly input without passing through the links in the relationships with other nodes among the nodes in the neural network. Alternatively, in the neural network, in the relationship between the nodes based on the link, the initial input node may mean nodes which do not have other input nodes connected through the links. Similarly thereto, the final output node may mean one or more nodes which do not have the output node in the relationship with other nodes among the nodes in the neural network. Further, a hidden node may mean nodes constituting the neural network other than the initial input node and the final output node.

In the neural network according to an embodiment of the present disclosure, the number of nodes of the input layer may be the same as the number of nodes of the output layer, and the neural network may be a neural network of a type in which the number of nodes decreases and then, increases again from the input layer to the hidden layer. Further, in the neural network according to another embodiment of the present disclosure, the number of nodes of the input layer may be smaller than the number of nodes of the output layer, and the neural network may be a neural network of a type in which the number of nodes decreases from the input layer to the hidden layer. Further, in the neural network according to still another embodiment of the present disclosure, the number of nodes of the input layer may be larger than the number of nodes of the output layer, and the neural network may be a neural network of a type in which the number of nodes increases from the input layer to the hidden layer. The neural network according to yet another embodiment of the present disclosure may be a neural network of a type in which the neural networks are combined.

A deep neural network (DNN) may refer to a neural network that includes a plurality of hidden layers in addition to the input and output layers. When the deep neural network is used, the latent structures of data may be determined. That is, latent structures of photos, text, video, voice, and music (e.g., what objects are in the photo, what the content and feelings of the text are, what the content and feelings of the voice are) may be determined. The deep neural network may include a convolutional neural network, a recurrent neural network (RNN), an auto encoder, generative adversarial networks (GAN), a restricted Boltzmann machine (RBM), a deep belief network (DBN), a Q network, a U network, a Siam network, a generative adversarial network (GAN), and the like. The description of the deep neural network described above is just an example and the present disclosure is not limited thereto.

In an embodiment of the present disclosure, the network function may include the auto encoder. The auto encoder may be a kind of artificial neural network for outputting output data similar to input data. The auto encoder may include at least one hidden layer and odd hidden layers may be disposed between the input and output layers. The number of nodes in each layer may be reduced from the number of nodes in the input layer to an intermediate layer called a bottleneck layer (encoding), and then expanded symmetrical to reduction to the output layer (symmetrical to the input layer) in the bottleneck layer. The auto encoder may perform non-linear dimensional reduction. The number of input and output layers may correspond to a dimension after preprocessing the input data. The auto encoder structure may have a structure in which the number of nodes in the hidden layer included in the encoder decreases as a distance from the input layer increases. When the number of nodes in the bottleneck layer (a layer having a smallest number of nodes positioned between an encoder and a decoder) is too small, a sufficient amount of information may not be delivered, and as a result, the number of nodes in the bottleneck layer may be maintained to be a specific number or more (e.g., half of the input layers or more).

The neural network may be learned in at least one scheme of supervised learning, unsupervised learning, semi supervised learning, or reinforcement learning. The learning of the neural network may be a process in which the neural network applies knowledge for performing a specific operation to the neural network.

The neural network may be learned in a direction to reduce or minimize errors of an output. The learning of the neural network is a process of repeatedly inputting learning data into the neural network and calculating the output of the neural network for the learning data and the error of a target and back-propagating the errors of the neural network from the output layer of the neural network toward the input layer in a direction to reduce the errors to update the weight of each node of the neural network. In the case of the supervised learning, the learning data labeled with a correct answer is used for each learning data (e.g., the labeled learning data) and in the case of the unsupervised learning, the correct answer may not be labeled in each learning data. That is, for example, the learning data in the case of the supervised learning related to the data classification may be data in which category is labeled in each learning data. The labeled learning data is input to the neural network, and the error may be calculated by comparing the output (category) of the neural network with the label of the learning data. As another example, in the case of the unsupervised learning related to the data classification, the learning data as the input is compared with the output of the neural network to calculate the error. The calculated error is back-propagated in a reverse direction (e.g., a direction from the output layer toward the input layer) in the neural network and connection weights of respective nodes of each layer of the neural network may be updated according to the back propagation. A variation amount of the updated connection weight of each node may be determined according to a learning rate. Calculation of the neural network for the input data and the back-propagation of the error may constitute a learning cycle (epoch). The learning rate may be applied differently according to the number of repetition times of the learning cycle of the neural network. For example, in an initial stage of the learning of the neural network, the neural network ensures a certain level of performance quickly by using a high learning rate, thereby increasing efficiency and uses a low learning rate in a latter stage of the learning, thereby increasing accuracy.

In learning of the neural network, the learning data may be generally a subset of actual data (e.g., data to be processed using the learned neural network), and as a result, there may be a learning cycle in which errors for the learning data decrease, but the errors for the actual data increase. Overfitting is a phenomenon in which the errors for the actual data increase due to excessive learning of the learning data. For example, a phenomenon in which the neural network that learns a cat by showing a yellow cat sees a cat other than the yellow cat and does not recognize the corresponding cat as the cat may be a kind of overfitting. The overfitting may act as a cause which increases the error of the machine learning algorithm. Various optimization methods may be used in order to prevent the overfitting. In order to prevent the overfitting, a method such as increasing the learning data, regularization, dropout of omitting a part of the node of the network in the process of learning, utilization of a batch normalization layer, etc., may be applied.

Figure 3:
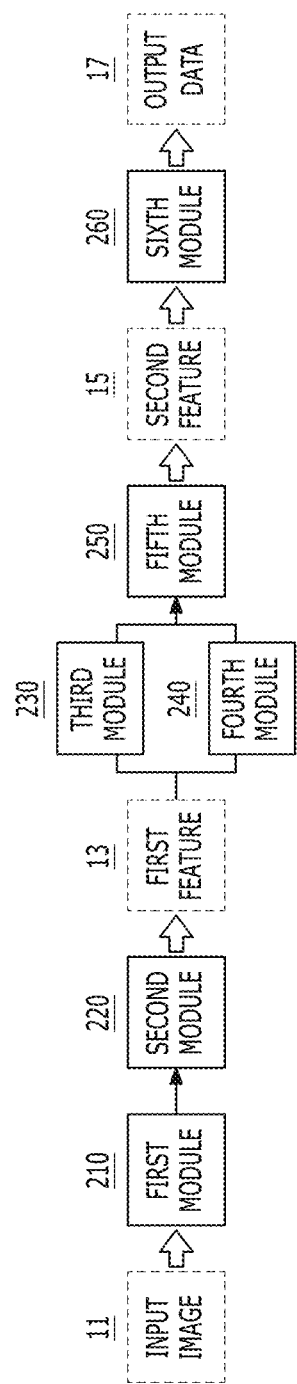
FIG. 3 is a block diagram illustrating modules which are included in the computing device and perform functions for evaluating a lesion according to the embodiment of the present disclosure.

FIG. 3 is a block diagram illustrating modules which are included in the computing device and perform functions for evaluating a lesion according to the embodiment of the present disclosure.

Referring to FIG. 3, the processor 110 of the computing device 100 according to the embodiment of the present disclosure may include a first module 210 for receiving an input image 11 and extracting a tile. In this case, the input image 11 may be a pathology slide image including tissue, such as the prostate. Further, the tile may also be a pixel of a basic configuration unit of the input image 11 or may also be a set of pixels. For example, as can be confirmed in FIG.

4, the first module 210 may extract a plurality of tiles 11-1, 11-2, . . . , and 11-N included in the input image 11 by using a pre-trained artificial neural network.

The processor 110 may include a second module 220 for receiving the plurality of tiles extracted through the first module 210 and extracting a feature for each tile. For example, the second module 220 may derive a first feature 13 of each tile by using the pre-trained artificial neural network. Meanwhile, the first feature 13 may include a feature for an image divided with a tile level. For example, the first feature 13 may mean the image divided of the tile level itself. Further, the first feature 13 may include a feature for an object (tissue, lesion, and the like) included in the image divided of the tile level, meta data or attribute data related to the image divided of the tile level, and the like, and may include various information for the image divided of the tile level in addition to the information.

The processor 110 may include at least one of a third module 230 and a fourth module 240 which receive the first feature 13 for each tile extracted through the second module 220 and evaluate the tissue present in the input image 11 for each tile. For example, the third module 230 may predict whether the lesion is present (for example, a tumor is present in the prostate tissue) for each tile based on the first feature 13 for each tile by using the pre-trained artificial neural network. In addition, the fourth module 240 may predict a pattern of the lesion (for example, the Gleason pattern) for each tile based on the first feature 13 for each tile by using the pre-trained artificial neural network. Further, the processor 110 may output a result of the prediction of each of the third module 230 and the fourth module 240 as an evaluation result for each tile. Further, the processor 110 may process the operations of the third module 230 and the fourth module 240 in parallel. Meanwhile, FIG. 3 illustrates that one third module 230 and one fourth module 240 operate, but each of the number of third modules 230 and the number of fourth modules 240 may be N as needed (N is a natural number).

The neural network included in each of the third module 230 and the fourth module 240 may be trained by receiving at least one of labeling data that is easily predicted and labeling data that is difficult to be predicted. For example, the neural network of the fourth module 240 may be trained by receiving labeling data that is easily predicted because the Gleason pattern is uniformly distributed, such as 3+3, 4+4. Further, the neural network of the fourth module 240 may also be trained by receiving labeling data that is difficult to be predicted because the Gleason pattern is not uniformly distributed, such as 3+4, 4+3. Further, the neural network of the fourth module 240 may also be trained by receiving training data consisting of the labeling data that is easily predicted and the labeling data that is difficult to be predicted.

Each of the third module 230 and the fourth module 240 may also be trained by the weakly supervised learning method. For example, the third module 230 may be trained based on a loss function that compares an average of first probability values representing whether a lesion is present in the plurality of tiles included in a predetermined medical image and a probability value labeled to the predetermined medical image (a probability value labeled at the image level) without tile-level labeling. Further, the fourth module may be trained by calculating the loss function for the tiles satisfying a predetermined reference (for example, the lesion presence probability) between the medical images having the corresponding patterns of the lesion at the image level (for example, between the medical images having the corresponding major and minor Gleason patterns) without tile-level labeling.

The processor 110 may include a fifth module 250 which combines an output of the third module 230 and an output of the fourth module 240. For example, the fifth module 250 may derive a second feature 15 for the entire input image 11 by integrating a result of the prediction for the presence or absence of the lesion for each tile (for example, whether the tumor is present in the prostate tissue for each tile) that is the output of the third module 230 and a result of the prediction for the pattern of the lesion for each tile (for example, the Gleason pattern for each tile) that is the output of the fourth module 240 by using the pre-trained artificial neural network. That is, the fifth module 250 may output the second feature 15 representing the feature for the entire input image 11 by combining the results of the prediction using the first feature 13 corresponding to the feature for each tile through the pre-trained artificial neural network.

The processor 110 may include a sixth module 260 which receives the second feature 15 derived through the fifth module 250 and calculates a result of an evaluation for the entire tissue present in the input image 11. For example, the sixth module 260 may predict an evaluation score of the lesion (for example, the Gleason grade of the prostate) present in the input image 11 based on the second feature 15 representing the feature for the entire input image 11 by using the pre-trained artificial neural network. That is, the sixth module 260 may generate the Gleason grade that is based on the entire prostate tissue as output data 17 based on the second feature 15 by using the pre-trained artificial neural network.

Since the computing device 100 including the foregoing modules 210 to 260 according to the embodiment of the present disclosure does not have a limitation in the type and the number of training data and the like, compared to the related art, it is possible to provide an accurate result value for the diagnosis of the lesion by using more diverse and more learning data. Further, since the computing device 100 is capable of providing a user with an interpretable evaluation result for each area, it is possible to effectively configure quantitative information and qualitative information for diagnosis of a lesion and to improve efficiency of the diagnosis of the lesion.

Figure 5:
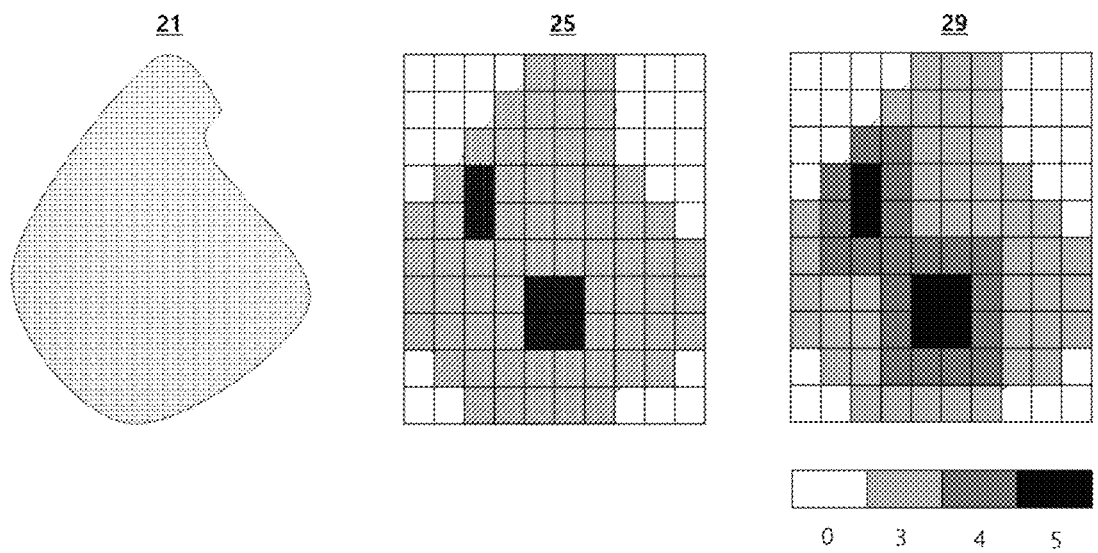
FIG. 5 is a conceptual diagram illustrating a lesion evaluation result of the computing device according to the embodiment of the present disclosure.

FIG. 5 is a conceptual diagram illustrating a lesion evaluation result of the computing device according to the embodiment of the present disclosure.

Figure 4:
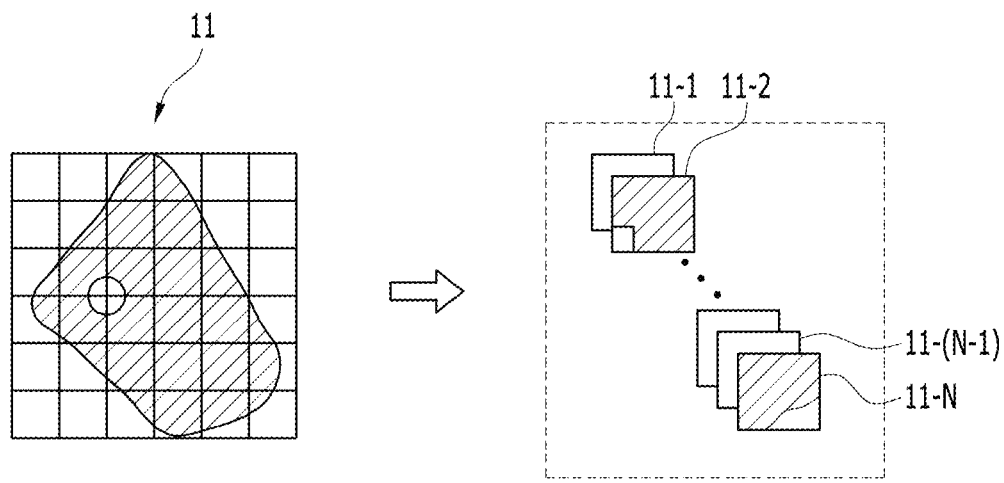
FIG. 4 is a conceptual diagram illustrating extraction of tiles from an input image according to the embodiment of the present disclosure.

Referring to FIG. 5, a left image 21 represents a pathology slide image to be input to the computing device 100 according to the embodiment of the present disclosure. The left image 21 includes a prostate tissue stained through hematoxylin and eosin (H&E). A middle image 25 represents a result of a prediction of presence or absence of a tumor in the prostate tissue for each tile of the left image 21. In the middle image 25, the tile predicted to have no tumor and the tile predicted to have tumors may be distinguished and displayed with different patterns or different colors. A right image 29 represents a result of the prediction of the Gleason pattern for each tile of the left image 21. In the right image 29, for each tile, a color may be distinguished and displayed according to the Gleason pattern. For example, when the color is set to gradually darken as the Gleason pattern increases to 0, 3, 4, and 5 like the color change bar arranged at the lowermost bottom of FIG. 4, each of the tiles corresponding to the prostate tissue in the right image 29 may be displayed in accordance with the color matched to the result of the prediction. However, the description related to the color change is simply one example, and the present disclosure is not limited thereto. The computing device 100 may distinguish the result of the prediction for each tile by color like the middle image 25 and the right image 29 and provide a user terminal with the result of the prediction for each tile in order to improve efficiency of diagnosis of the prostate cancer.

Figure 6:
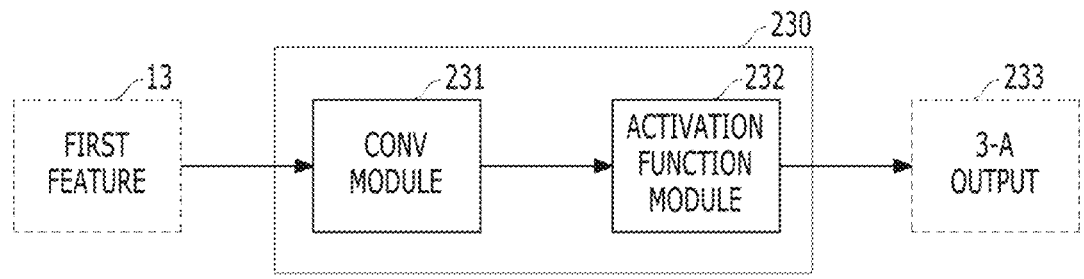
FIG. 6 is a configuration diagram illustrating an example of configurations of a third module according to the embodiment of the present disclosure.

FIG. 6 is a configuration diagram illustrating an example of configurations of the third module 230 according to the embodiment of the present disclosure.

Referring to FIG. 6, the third module 230 according to the embodiment of the present disclosure may analyze presence and absence of the lesion (for example, presence and absence of the tumor in the prostate tissue) for each tile based on the first feature 13 for each tile by using the pre-trained artificial neural network. Further, the third module 230 may include a Cony module 231 for applying a convolution operation to the first feature 130 for each tile, and an activation function module 232 for applying an activation function after the application of the convolution operation, and output a result (3-A output) of the prediction of the presence or absence of the lesion for each tile.

Here, the Cony module 231 is the module for applying the convolution operation to the first feature 130 for each tile. For example, the Cony module 231 may apply a 1×1 convolution operation to the first feature for each tile.

The activation function module 232 is the module for applying the activation function to a result to which the convolution operation is applied. For example, the activation function module 232 may apply a sigmoid function to a result to which the 1×1 convolution operation is applied. Further, the activation function module 232 may also apply a SoftMax function and the like for generating various output values.

The result (3-A output) of the prediction of the presence or absence of the tumor in the prostate tissue for each tile may include data representing a probability of the presence of the lesion for each tile. The data may be binary data (presence/absence) or particular numerical value data.

The third module 230 may generate a map representing the presence or absence of the lesion for each tile (for example, the presence or absence of the tumor in the prostate tissue for each tile) based on the operation operations. For example, the third module 230 may generate a map in which the tile predicted to have no lesion and the tile predicted to have the lesion are expressed with different patterns, like the middle image 25 of FIG. 5. Further, the third module may also generate a heat map in which a probability value of each value is expressed by progress color distinguishment.

Figure 7:
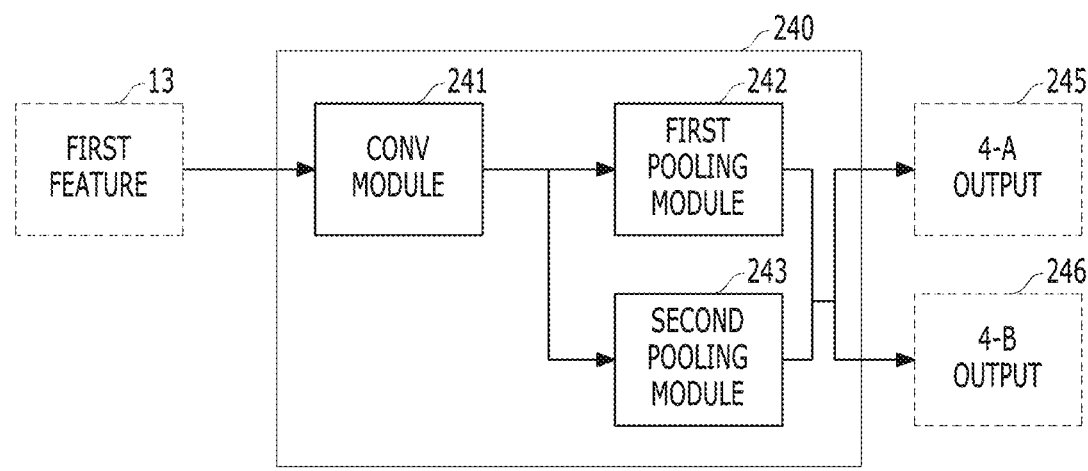
FIG. 7 is a configuration diagram illustrating an example of configurations of a fourth module according to the embodiment of the present disclosure.

FIG. 7 is a configuration diagram illustrating an example of configurations of a fourth module according to the embodiment of the present disclosure.

Referring to FIG. 7, the fourth module 240 according to the embodiment of the present disclosure may analyze the pattern of the lesion (for example, the Gleason pattern) for each tile based on the first feature 13 for each tile by using the pre-trained artificial neural network. Further, the fourth module 240 may include a Cony module 241 for applying a convolution operation to the first feature 130 for each tile, and a first pooling module 242 and a second pooling module 245 for performing pooling operations in parallel after the convolution operation is applied, and generate the plurality of outputs (4-A output and 4-B output) related to the pattern of the lesion for each tile.

Herein, the Cony module 241 is the module for applying the convolution operation to the first feature 130 for each tile. For example, the Cony module 241 may apply 1×1 convolution operations to the first feature for each tile as many as the number of Gleason pattern classes. In particular, the Cony module 241 may perform four 1×1 convolution operations when the glasses of the Gleason pattern is 4 (for example, when the Gleason pattern is distinguished into four glasses {0, 1, 2, 3}).

Further, the first pooling module 242 and the second pooling module 243 may perform pooling operations for the result output from the Cony module in parallel. For example, the first pooling module 242 may apply a max pooling operation to the result output by the Cony module, and the second pooling module 243 may apply an average pooling operation to the result output by the Cony module 241. Further, a result of the max polling operation and a result of the average pooling operation may be combined, and the plurality of outputs (4-A and 4-B) related to the pattern of the lesion for each tile may be generated based on the combined result. Meanwhile, according to the embodiment, the plurality of outputs (4-A and 4-B) may also be individually generated based on at least one of the result of the max pooling operation and the result of the average pooling operation.

Meanwhile, the fourth module 240 may generate a map representing the pattern of the lesion (for example, the Gleason pattern) for each tile of the input image 11 based on the output of the second pooling module 243 and the 4-B output. For example, the fourth module 240 may generate a heat map in which the pattern of the lesion for each tile of the input image 11 is expressed by progressive color distinguishment like the right image 29 of FIG. 5. Further, the heat map expressing the pattern of the lesion for each tile may be provided to the user as an additional output separate from the result of the prediction for the entire input image 11.

Figure 8:
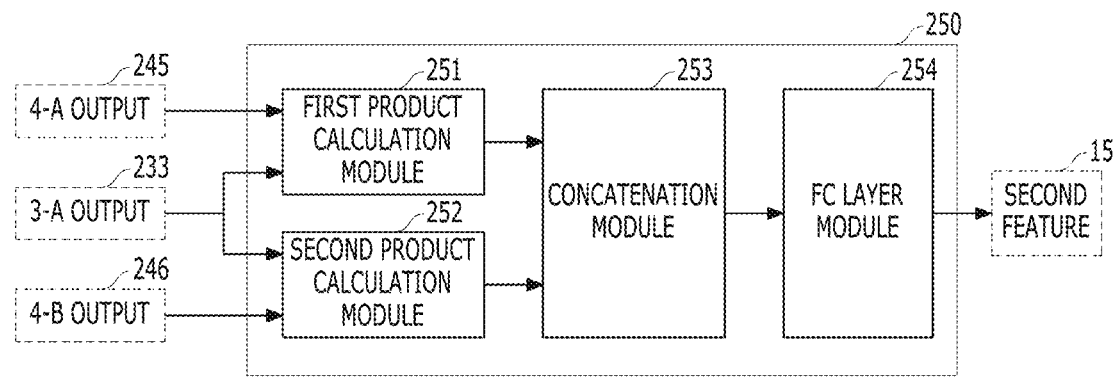
FIG. 8 is a configuration diagram illustrating an example of configurations of a fifth module according to the embodiment of the present disclosure.

FIG. 8 is a configuration diagram illustrating an example of configurations of the fifth module 250 according to the embodiment of the present disclosure.

Referring to FIG. 8, the fifth module 250 according to the embodiment of the present disclosure may combine the output of the third module 230 and the output of the fourth module 240. For example, the fifth module 250 may combine the result (the 3-A output) of the prediction of the presence or absence of the lesion (for example, the presence or absence of the tumor in the prostate tissue) for each tile that is the output of the third module 230 and the result (the 4-A output and the 4-B output) of the prediction of the pattern of the lesion (for example, the Gleason pattern) for each tile that is the output of the fourth module 240 by using the pre-trained artificial neural network, and derive the second feature 15 for the entire input image 11 through the combined result. Further, the fifth module 250 may include a first product calculation module 251, a second product calculation module 252, a concatenation module 253, and an FC layer module 254 for the operations.

Herein, the first product calculation module 251 and the second product calculation module 252 are the configurations performing the product operation between the result (the 3-A output) of the prediction of the presence or absence of the lesion for each tile that is the output of the third module 230 and the result (the 4-A output and the 4-B output) of the prediction of the pattern of the lesion for each tile that is the output of the fourth module 240. For example, the first product calculation module 251 performs the product operation between the 3-A output and the 4-A output, and the second product calculation module 252 performs the product operation between the 3-A output and the 4-B output.

The concatenation module 253 is the configuration performing a concatenation operation on the results of the first product calculation module 251 and the second product calculation module 252.

The FC layer module 254 performs a calculation operation in a Fully Connected (FC) layer on the output of the concatenation module 253, and may derive the second feature 15 for the entire input image 11 through the calculation operation.

Meanwhile, the second feature 15 derived by the fifth module 250 may be transmitted to the sixth module 260 described above, and may be utilized for predicting an evaluation score of the lesion present in the input image 11 (for example, the Gleason grade of the prostate).

Figure 9:
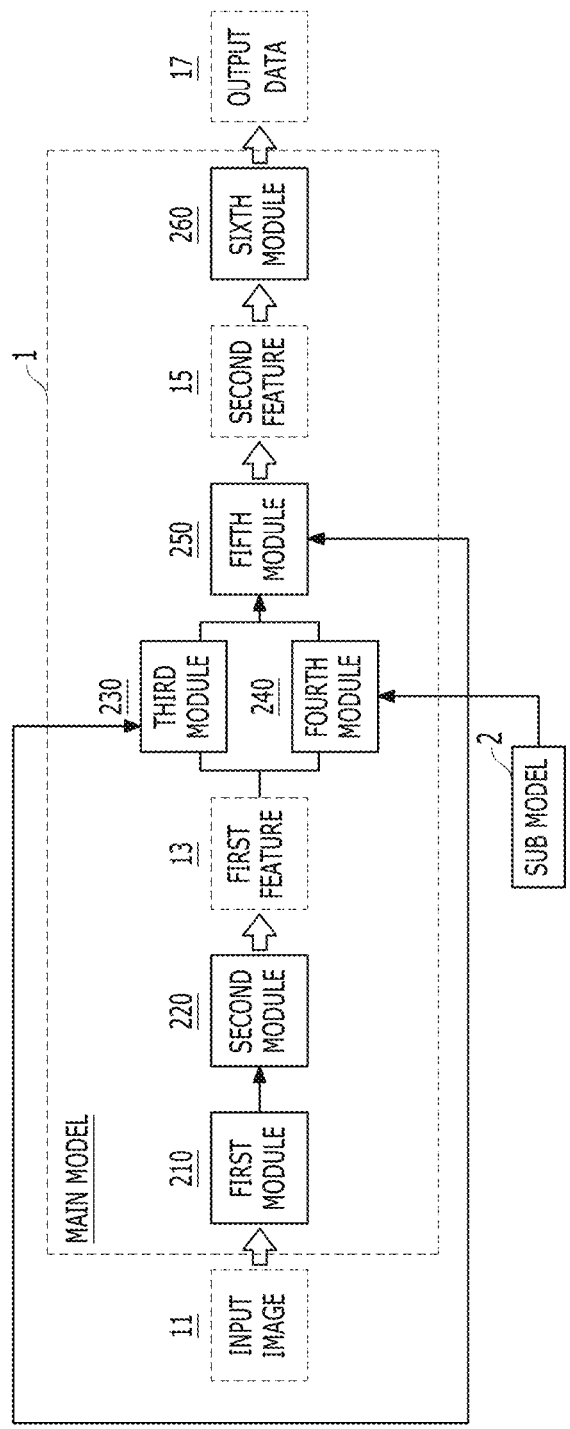
FIGS. 9 and 10 are block diagrams illustrating other examples of modules which are included in the computing device and perform functions for evaluating a lesion according to the embodiment of the present disclosure.

FIG. 9 is a block diagram illustrating other examples of modules which are included in the computing device and perform functions for evaluating a lesion according to the embodiment of the present disclosure.

Referring to FIG. 9, the computing device may additionally include a sub model 2 for correcting the modules included in a main model 1 and improving performance.

The main model 1 may include the first module 210, the second module 220, the third module 230, the fourth module 240, the fifth module 250, the sixth module 260, and the like which have been described above, and the sub model 2 may perform an operation for correcting at least one model included in the main model 1.

In particular, the sub model 2 may perform an operation of correcting the output of the third module 230, the output of the fourth module 240, and the like, which has a relatively large influence on the performance of lesion analysis. For example, the sub model 2 may generate an additional probability value (for example, a second probability value) for the presence or absence of the lesion (for example, the presence or absence of the tumor in the prostate tissue) for each tile of the plurality of tiles of the input image 11, and help the generated additional probability value to be utilized for the correction of the 3-A output 233 of the third module 230, the 4-B output 246 of the fourth module 240, and the like. Meanwhile, the 3-A output 233 and the 4-B output 246 are the information directly utilized for deriving the second feature 15 for the entire input image 11, and the 3-A output 233 is the information directly utilized for generating heat map information for the lesion pattern (for example, the Gleason pattern), so that the outputs of the main model may be improved through the correction of the data.

The sub model 2 may include a ResNext model and the like and perform a classification operation for each tile, and generate an additional probability value for each tile.

The sub model 2 may be trained by a supervised learning method utilizing label, and through this, it is possible to give an effect of additional performance improvement even when some modules of the main model are not trained by the supervised learning method (for example, when some modules of the main model are trained by the weakly supervised learning method).

Figure 10:
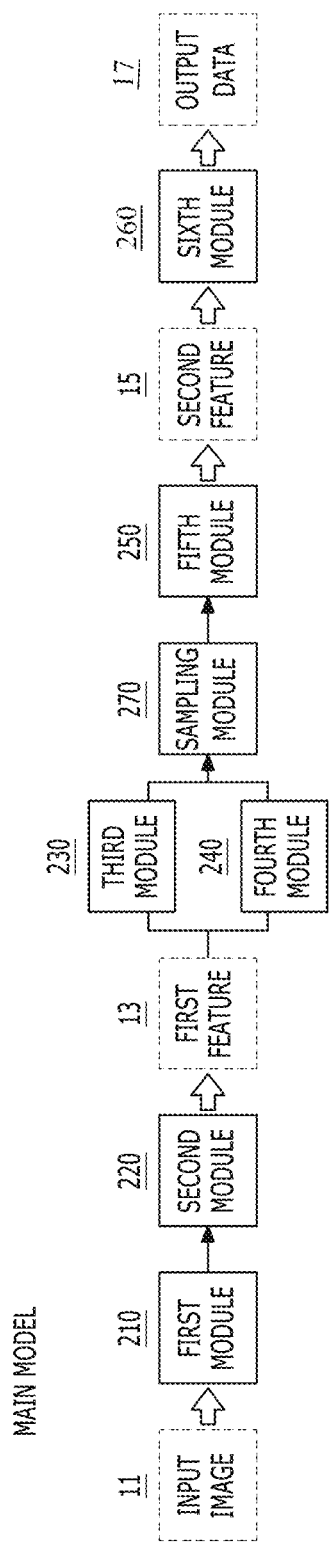

FIG. 10 is a block diagram illustrating other examples of modules which are included in the computing device and perform functions for evaluating a lesion according to the embodiment of the present disclosure.

Referring to FIG. 10, the computing device may additionally include a sampling module 270 performing a sampling operation after the operation of the third module 230 and the operation of the fourth module 240.

The sampling module 270 may perform a sampling operation by a random sampling method, and in addition to the foregoing method, the sampling module 270 may utilize various sampling methods.

The sampling module 270 may sample K tiles among the plurality of tiles 11-1, 11-1, . . . , and 11-N of the input image 11, and extract "data for the presence or absence of the lesion (for example, the presence or absence of the tumor in the prostate tissue) for each tile" for the K sampled tiles (for example, 32 tiles) and "data for the pattern of the lesion (for example, the Gleason pattern) for each tile." For example, the sampling module 270 may extract data for the K sampled tiles from the output (3-A output) of the third module 230 and generate sampled output (for example, 3-A-sampling output), and extract data for the K sampled tiles from the outputs (4-A and 4-B) of the fourth module 240 and generate sampled outputs (4-A-sampling and 4-B-sampling outputs), and the sampled outputs may be utilized in the fifth module 250.

The sampling module 270 may perform the plurality of sampling operations, and transmit the plurality of sets of sampled data to the fifth module 250. For example, the sampling module 270 may perform the random sampling operations on the K tiles m times, and transmit m data sets including the sampling data for the K tiles to the fifth module 250. In this case, the fifth module 250 and the sixth module 260 may generate m second features 15 and generate m lesion evaluation scores (for example, the Gleason grade) by utilizing the received m data sets, and determine a final output by applying an ensemble methods (for example, an average and a mode) on the m generated data.

Meanwhile, when the sampling module 270 is added, dependency on the input image 11 may be decreased. In particular, by adding the sampling module 270, the "input image 11 (for example, the entire image at the slide level)" is different from the "image utilized for the final output (the sampled image of the tile level)," so that dependency on the input image may be decreased in the analysis/prediction stage, and high analysis/prediction performance may be guaranteed even for various types of medical images.

Figure 11:
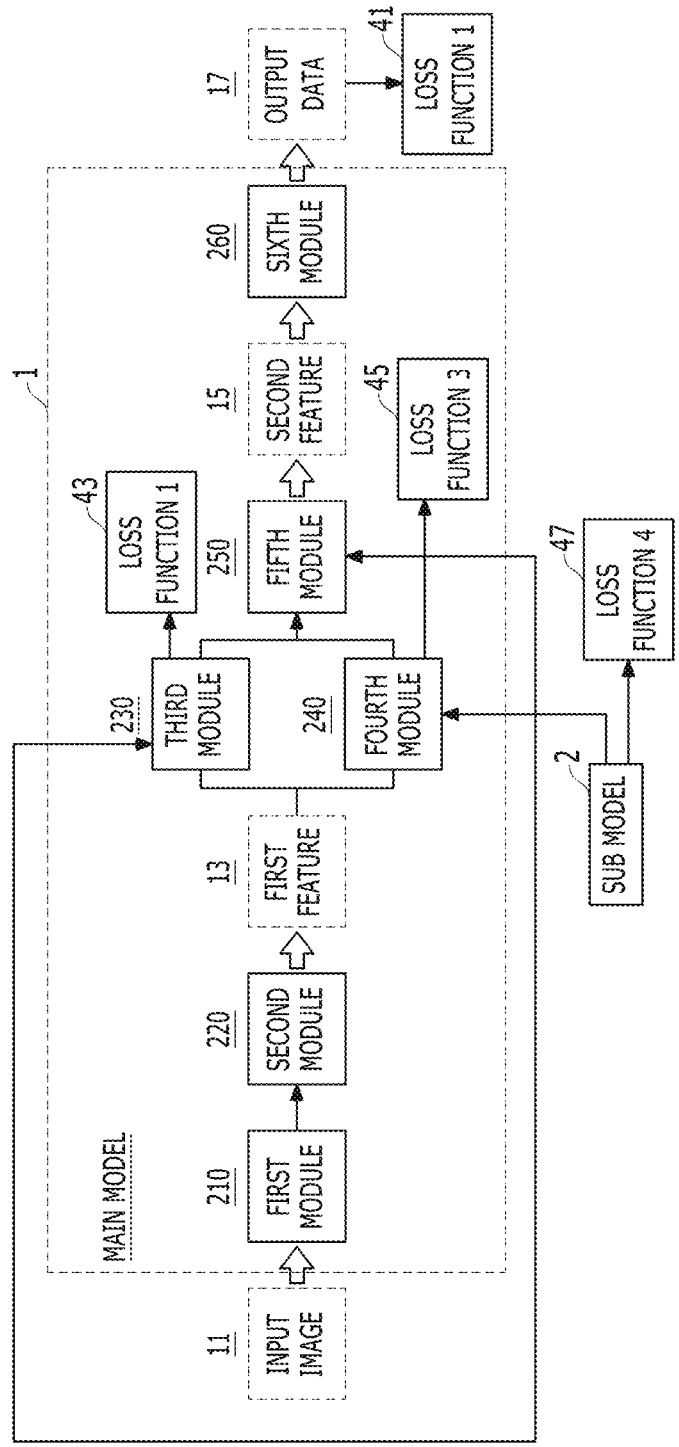
FIG. 11 is a conceptual diagram illustrating loss functions according to the embodiment of the present disclosure.

FIG. 11 is a conceptual diagram illustrating loss functions according to the embodiment of the present disclosure.

Referring to FIG. 11, the main model 1 and the sub model 2 according to the embodiment of the present disclosure may be trained based on the plurality of loss functions. For example, the main model 1 may be trained based on the first loss function 41, the second loss function 43, the third loss function 45, and the like, and the sub model 2 may be trained based on the fourth loss function 47 and the like.

The first loss function 41 is the configuration for calculating a loss value based on the output data 17. For example, the first loss function 41 is the configuration for calculating a loss value between the predicted evaluation score of the lesion for the predetermined image (for example, the predicted Gleason grade for the entire image) and the data labeled to the predetermined image. The first loss function 41 may be utilized for the supervised learning at the entire image level. Meanwhile, when the sampling module 270 is added, the first loss function 41 may be configured to calculate a loss value between the predicted evaluation score of the lesion based on the sampled tiles (for example, the predicted Gleason grade for the entire image based on the sampled tiles) and the data labeled to the predetermined image.

The second loss function 43 is the configuration for calculating a loss value based on the output of the third module 230. The second loss function 43 may calculate a loss value for training the outputs of the tile level by the weakly supervised learning method without tile-level labeling. For example, the second loss function 43 may calculate a loss value between an average of first probability values representing the presence or absence of the lesion (for example, the presence or absence of the tumor in the prostate tissue) of the plurality of tiles included in the predetermined image and a probability value labeled to the predetermined image (the labeled probability value at the image level) without tile-level labeling, and the weakly supervised learning of the output of the third module 230 may be performed based on the loss value. Meanwhile, when the sampling module 270 is added, the second loss function 43 may be configured to calculate a loss value between the average of the first probability values for the sample tiles and the probability value labeled to the predetermined image.

The third loss function 45 is the configuration for calculating a loss value based on the output of the fourth module 240. The third loss function 45 may calculate a loss value for training the model with the outputs of the tile level by the weakly supervised learning method without tile-level labeling. For example, the third loss function 45 may calculate a loss value for the tiles satisfying the predetermined reference (for example, the tiles in which the tumor probability exceeds the specific threshold value) between the medical images having the corresponding patterns of the lesion at the image level (for example, between the medical images having the corresponding major and minor Gleason patterns) without tile-level labeling, and the weakly supervised learning for the output of the fourth module 240 may be performed based on the loss value. Meanwhile, when the sampling module 270 is added, the third loss function 45 may be configured to calculate a loss value for the tiles satisfying the predetermined reference between the medical images having the corresponding Gleason patterns in the range of the sampled tiles.

The fourth loss function 47 is the configuration for calculating a loss value based on the output of the sub model 2. For example, the fourth loss function 47 is the configuration for calculating a loss value between an additional probability value (for example, the second probability value) for the presence or absence of the lesion for each tile (for example, the presence or absence of the tumor in the prostate tissue) and the data labeled of the tile level. Further, the second probability value and the labeled data may be binary classification values (benign/malignant) or particular numerical values. The fourth loss function 47 may be utilized for the supervised learning of the output of the sub model 2. Meanwhile, the fourth loss function 47 may perform the learning assisting the second loss function 43 or the third loss function 45 even though the second loss function 43 or the third loss function 45 is not implemented in the form for the supervised learning.

Figure 12:
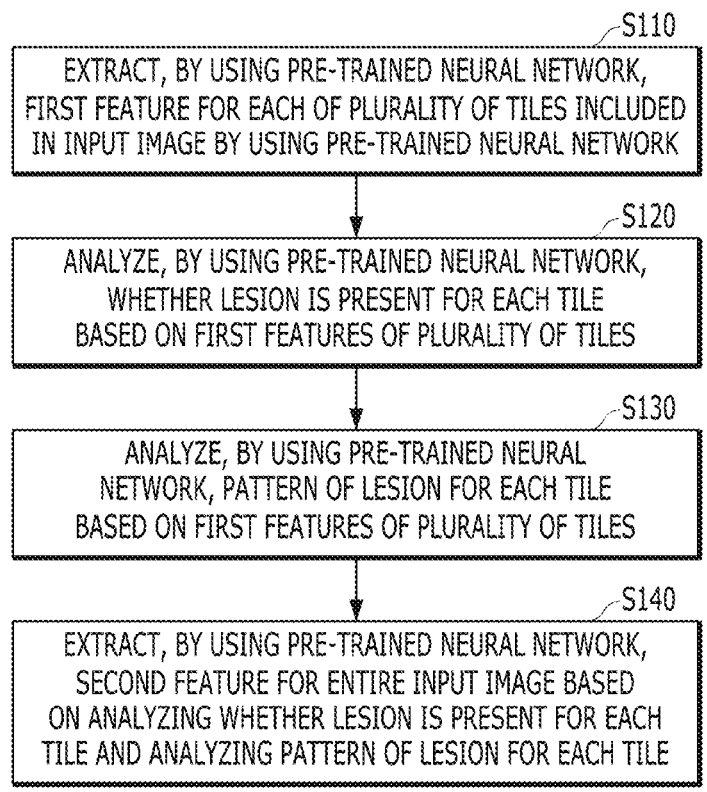
FIG. 12 is a flowchart illustrating a method of analyzing a lesion based on a medical image according to the embodiment of the present disclosure.

FIG. 12 is a flowchart illustrating a method of analyzing a lesion based on a medical image according to the embodiment of the present disclosure.

The method of analyzing the lesion based on the medical image may be implemented or performed by the modules of the computing device which have been described above.

Referring to FIG. 12, the method of analyzing the lesion based on the medical image may include: extracting a first feature of each of a plurality of tiles included in an input image by using a pre-trained artificial neural network (S110); analyzing whether a lesion is present for each tile based on the first feature of the plurality of tiles by using the pre-trained artificial neural network (S120); analyzing a pattern of the lesion for each tile based on the first feature of the plurality of tiles by using the pre-trained artificial neural network (S130); and extracting a second feature for the entire input image based on the analyzing of whether the lesion is present for each tile and the analyzing of the pattern of the lesion for each tile by using the pre-trained artificial neural network (S140).

Herein, operation S110 may be implemented based on, for example, the operations of the first module 210, the second module 220, and the like which have been described above. Further, operation S120 may be implemented based on, for example, the operations of the third module 230 which has been described above. Further, operation S130 may be implemented based on, for example, the operations of the fourth module 240 which has been described above. Further, operation S140 may be implemented based on, for example, the operations of the fifth module 250 which has been described above.

In the method of analyzing the lesion based on the medical image, the input image may be the image including the prostate tissue, the pattern of the lesion may correspond to the Gleason pattern, and the method of analyzing the lesion based on the medical image may further include determining a prostate cancer score for the entire input image based on the second feature by using the pre-trained artificial neural network after operation S140.

Operation S140 may include: sampling some of the plurality of tiles; and extracting the second feature based on analysis data representing whether the lesion is present for the sampled tiles and analysis data representing the pattern of the lesion for the sampled tiles by using the pre-trained artificial neural network. Meanwhile, when the sampling operation is added, a technical effect of decreasing dependency on the input image may be implemented. For example, by adding the sampling operation, the "input image (for example, the entire image at the slide level)" is different from the "image utilized for the final output (the sampled image of the tile level)," so that dependency on the input image may be decreased in the analysis/prediction operations, and high analysis/prediction performance may be guaranteed even for various types of medical images.

Operations S120 and S130 may be performed in an encoder part of the pre-trained artificial neural network, and operation S140 may be performed in a decoder part of the pre-trained artificial neural network. For example, when the pre-trained artificial neural network includes a main model for implementing the operations of the first module 210, the second module 220, the third module 230, the fourth module 240, the fifth module 250, and the sixth module 260 as described above, operation S120 and S130 may be implemented by the operations of the third module 230 and the fourth module 240 which may be substantially included in the encoder part of the main model, and operation S140 may be implemented by the operations of the fifth module 250 which may be substantially included in the decoder part of the main model.

The method of analyzing the lesion based on the medical image may include determining an evaluation score of the lesion for the entire input image based on the second feature by using the pre-trained artificial neural network. In this case, the pre-trained artificial neural network may include a main model trained based on a comparison between an evaluation score determined for a predetermined image and a score labeled to the predetermined image.

The main model utilized for implementing the method of analyzing the lesion based on the medical image may be additionally trained based on a comparison between an average of first probability values representing whether the lesion is present in the plurality of tiles included in the predetermined image and a probability value labeled to the predetermined image without tile-level labeling.

Operation S120 may include: determining a first probability value representing whether the lesion is present for each tile of the plurality of tiles by using the main model; determining a second probability value representing whether the lesion is present for each tile of the plurality of tiles by using a sub model of the pre-trained artificial neural network; and correcting the first probability value based on the second probability value. In this case, the sub model may be trained based on labeling of the tile level.

The main model utilized for implementing the method of analyzing the lesion based on the medical image may be additionally trained by comparing patterns of the lesion of the tiles satisfying a predetermined reference between the images having corresponding patterns of the lesion at an image level without tile-level labeling.

Operation S130 may include: determining a probability value representing whether the lesion is present for each tile of the plurality of tiles by using the sub model of the pre-trained artificial neural network; and correcting the pattern of the lesion for each tile based on the probability value. In this case, the sub model may be trained based on labeling of the tile level.

The method of analyzing the lesion based on the medical image may additionally include operations for providing a plurality of outputs to be provided to a user. For example, the method of analyzing the lesion based on the medical image may further include outputting a map (for example, a heat map) representing the pattern (for example, the Gleason pattern) of the lesion included in the input image as a first output based on operation S130. Further, the method of analyzing the lesion based on the medical image may further include determining an evaluation score of the lesion for the entire input image based on the second feature by using the pre-trained artificial neural network and outputting the determined evaluation score of the lesion as a second output, after operation S140. Further, the method of analyzing the lesion based on the medical image may further include outputting an additional map representing a probability of the presence of the lesion for each tile of the input image as a third output based on operation S120.

Figure 13:
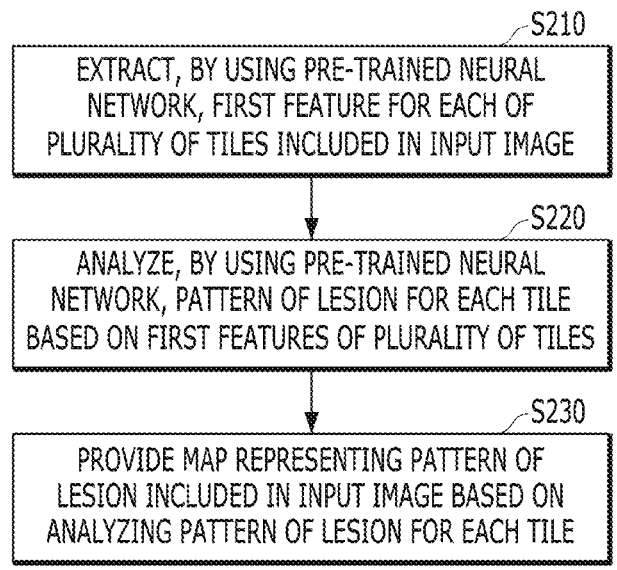
FIG. 13 is a flowchart illustrating another example of the method of analyzing the lesion based on the medical image according to the embodiment of the present disclosure.

FIG. 13 is a flowchart illustrating another example of the method of analyzing the lesion based on the medical image according to the embodiment of the present disclosure.

The method of analyzing the lesion based on the medical image may be implemented or performed by the modules of the computing device which have been described above.

Referring to FIG. 13, the method of analyzing the lesion based on the medical image may include: extracting a first feature of each of a plurality of tiles included in an input image by using a pre-trained artificial neural network (S210); analyzing a pattern of a lesion for each tile based on the first feature of the plurality of tiles by using the pre-trained artificial neural network (S220); and providing a map representing a pattern of the lesion included in the input image based on the analyzing of the pattern of the lesion for each tile (S230).

In this case, operation S220 may be performed by a model trained without tile-level labeling. Further, the model trained without tile-level labeling may be a model trained by comparing patterns of the tiles satisfying a predetermined reference between images having corresponding patterns of the lesion at an image level. That is, the method of analyzing the lesion based on the medical image may provide a map representing the pattern of the lesion of the tile level by utilizing the weakly supervised learning method in a tile level prospective.

Operation S210 may be implemented based on, for example, the operations of the first module 210, the second module 220, and the like which have been described above. Further, operations S220 and S230 may be implemented based on, for example, the operations of the fourth module 240 which have been described above.

The method of analyzing the lesion based on the medical image may further include: analyzing a probability of presence of the lesion of each of the plurality of tiles included in the input image by using a sub model; and correcting a result of the analysis of the pattern of the lesion for each tile based on the analyzing of the probability of the presence of the lesion of each of the plurality of tiles. Meanwhile, the sub model is the model trained based on the labeling of the tile level.

Meanwhile, the methods of analyzing the lesion based on the medical image may be implemented in the form of a program executable by a processor, and may be implemented in the form storable in a storage medium.

Figure 14:
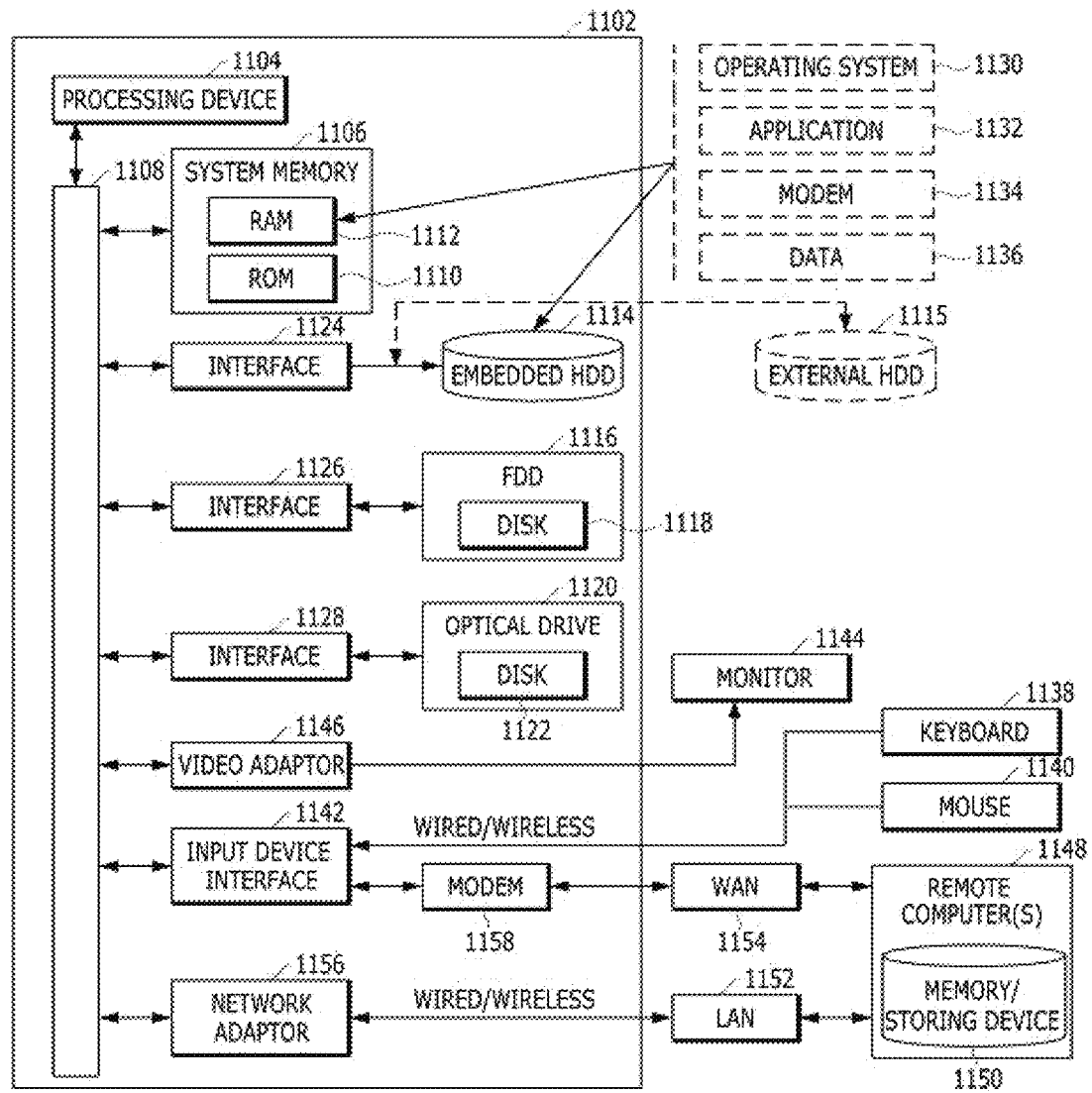
FIG. 14 is a block diagram of a computing device according to the embodiment of the present disclosure.

FIG. 14 is a simple and normal schematic view of a computing environment in which the embodiments of the present disclosure may be implemented.

It is described above that the present disclosure may be generally implemented by the computing device, but those skilled in the art will well know that the present disclosure may be implemented in association with a computer executable command which may be executed on one or more computers and/or in combination with other program modules and/or as a combination of hardware and software.

In general, the program module includes a routine, a program, a component, a data structure, and the like that execute a specific task or implement a specific abstract data type. Further, it will be well appreciated by those skilled in the art that the method of the present disclosure can be implemented by other computer system configurations including a personal computer, a handheld computing device, microprocessor-based or programmable home appliances, and others (the respective devices may operate in connection with one or more associated devices as well as a single-processor or multi-processor computer system, a mini computer, and a main frame computer.

The embodiments described in the present disclosure may also be implemented in a distributed computing environment in which predetermined (or selected) tasks are performed by remote processing devices connected through a communication network. In the distributed computing environment, the program module may be positioned in both local and remote memory storage devices.

The computer generally includes various computer readable media. Media accessible by the computer may be computer readable media regardless of types thereof and the computer readable media include volatile and non-volatile media, transitory and non-transitory media, and mobile and non-mobile media. As a non-limiting example, the computer readable media may include both computer readable storage media and computer readable transmission media. The computer readable storage media include volatile and non-volatile media, temporary and non-temporary media, and movable and non-movable media implemented by a predetermined (or selected) method or technology for storing information such as a computer readable instruction, a data structure, a program module, or other data. The computer readable storage media include a RAM, a ROM, an EEPROM, a flash memory or other memory technologies, a CD-ROM, a digital video disk (DVD) or other optical disk storage devices, a magnetic cassette, a magnetic tape, a magnetic disk storage device or other magnetic storage devices or predetermined (or selected) other media which may be accessed by the computer or may be used to store desired information, but are not limited thereto.

The computer readable transmission media generally implement the computer readable command, the data structure, the program module, or other data in a carrier wave or a modulated data signal such as other transport mechanism and include all information transfer media. The term "modulated data signal" means a signal obtained by configuring or changing at least one of characteristics of the signal so as to encode information in the signal. As a non-limiting example, the computer readable transmission media include wired media such as a wired network or a direct-wired connection and wireless media such as acoustic, RF, infrared and other wireless media. A combination of any media among the aforementioned media is also included in a range of the computer readable transmission media.

An environment 1100 that implements various aspects of the present disclosure including a computer 1102 is shown and the computer 1102 includes a processing device 1104, a system memory 1106, and a system bus 1108. The system bus 1108 connects system components including the system memory 1106 (not limited thereto) to the processing device 1104. The processing device 1104 may be a predetermined (or selected) processor among various commercial processors. A dual processor and other multi-processor architectures may also be used as the processing device 1104.

The system bus 1108 may be any one of several types of bus structures which may be additionally interconnected to a local bus using any one of a memory bus, a peripheral device bus, and various commercial bus architectures. The system memory 1106 includes a read only memory (ROM) 1110 and a random access memory (RAM) 1112. A basic input/output system (BIOS) is stored in the non-volatile memories 1110 including the ROM, the EPROM, the EEPROM, and the like and the BIOS includes a basic routine that assists in transmitting information among components in the computer 1102 at a time such as in-starting. The RAM 1112 may also include a high-speed RAM including a static RAM for caching data, and the like.

The computer 1102 also includes an interior hard disk drive (HDD) 1114 (for example, EIDE and SATA), in which the interior hard disk drive 1114 may also be configured for an exterior purpose in an appropriate chassis (not illustrated), a magnetic floppy disk drive (FDD) 1116 (for example, for reading from or writing in a mobile diskette 1118), and an optical disk drive 1120 (for example, for reading a CD-ROM disk 1122 or reading from or writing in other high-capacity optical media such as the DVD, and the like). The hard disk drive 1114, the magnetic disk drive 1116, and the optical disk drive 1120 may be connected to the system bus 1108 by a hard disk drive interface 1124, a magnetic disk drive interface 1126, and an optical drive interface 1128, respectively. An interface 1124 for implementing an exterior drive includes at least one of a universal serial bus (USB) and an IEEE 1394 interface technology or both of them.

The drives and the computer readable media associated therewith provide non-volatile storage of the data, the data structure, the computer executable instruction, and others. In the case of the computer 1102, the drives and the media correspond to storing of predetermined (or selected) data in an appropriate digital format. In the description of the computer readable media, the mobile optical media such as the HDD, the mobile magnetic disk, and the CD or the DVD are mentioned, but it will be well appreciated by those skilled in the art that other types of media readable by the computer such as a zip drive, a magnetic cassette, a flash memory card, a cartridge, and others may also be used in an operating environment and further, the predetermined (or selected) media may include computer executable commands for executing the methods of the present disclosure.

Multiple program modules including an operating system 1130, one or more application programs 1132, other program module 1134, and program data 1136 may be stored in the drive and the RAM 1112. All or some of the operating system, the application, the module, and/or the data may also be cached in the RAM 1112. It will be well appreciated that the present disclosure may be implemented in operating systems which are commercially usable or a combination of the operating systems.

A user may input instructions and information in the computer 1102 through one or more wired/wireless input devices, for example, pointing devices such as a keyboard 1138 and a mouse 1140. Other input devices (not illustrated) may include a microphone, an IR remote controller, a joystick, a game pad, a stylus pen, a touch screen, and others. These and other input devices are often connected to the processing device 1104 through an input device interface 1142 connected to the system bus 1108, but may be connected by other interfaces including a parallel port, an IEEE 1394 serial port, a game port, a USB port, an IR interface, and others.

A monitor 1144 or other types of display devices are also connected to the system bus 1108 through interfaces such as a video adapter 1146, and the like. In addition to the monitor 1144, the computer generally includes other peripheral output devices (not illustrated) such as a speaker, a printer, others.

The computer 1102 may operate in a networked environment by using a logical connection to one or more remote computers including remote computer(s) 1148 through wired and/or wireless communication. The remote computer (s) 1148 may be a workstation, a computing device computer, a router, a personal computer, a portable computer, a micro-processor based entertainment apparatus, a peer device, or other general network nodes and generally includes multiple components or all of the components described with respect to the computer 1102, but only a memory storage device 1150 is illustrated for brief description. The illustrated logical connection includes a wired/wireless connection to a local area network (LAN) 1152 and/or a larger network, for example, a wide area network (WAN) 1154. The LAN and WAN networking environments are general environments in offices and companies and facilitate an enterprise-wide computer network such as Intranet, and all of them may be connected to a worldwide computer network, for example, the Internet.

When the computer 1102 is used in the LAN networking environment, the computer 1102 is connected to a local network 1152 through a wired and/or wireless communication network interface or an adapter 1156. The adapter 1156 may facilitate the wired or wireless communication to the LAN 1152 and the LAN 1152 also includes a wireless access point installed therein in order to communicate with the wireless adapter 1156. When the computer 1102 is used in the WAN networking environment, the computer 1102 may include a modem 1158 or has other means that configure communication through the WAN 1154 such as connection to a communication computing device on the WAN 1154 or connection through the Internet. The modem 1158 which may be an internal or external and wired or wireless device is connected to the system bus 1108 through the serial port interface 1142. In the networked environment, the program modules described with respect to the computer 1102 or some thereof may be stored in the remote memory/storage device 1150. It will be well known that an illustrated network connection is and other means configuring a communication link among computers may be used.

The computer 1102 performs an operation of communicating with predetermined (or selected) wireless devices or entities which are disposed and operated by the wireless communication, for example, the printer, a scanner, a desktop and/or a portable computer, a portable data assistant (PDA), a communication satellite, predetermined (or selected) equipment or place associated with a wireless detectable tag, and a telephone. This at least includes wireless fidelity (Wi-Fi) and Bluetooth wireless technology. Accordingly, communication may be a predefined structure like the network in the related art or just ad hoc communication between at least two devices.

The wireless fidelity (Wi-Fi) enables connection to the Internet, and the like without a wired cable. The Wi-Fi is a wireless technology such as the device, for example, a cellular phone which enables the computer to transmit and receive data indoors or outdoors, that is, anywhere in a communication range of a base station. The Wi-Fi network uses a wireless technology called IEEE 802.11(a, b, g, and others) in order to provide safe, reliable, and high-speed wireless connection. The Wi-Fi may be used to connect the computers to each other or the Internet and the wired network (using IEEE 802.3 or Ethernet). The Wi-Fi network may operate, for example, at a data rate of 11 Mbps (802.11a) or 54 Mbps (802.11b) in unlicensed 2.4 and 5 GHz wireless bands or operate in a product including both bands (dual bands).

It will be appreciated by those skilled in the art that information and signals may be expressed by using various different predetermined (or selected) technologies and techniques. For example, data, instructions, commands, information, signals, bits, symbols, and chips which may be referred in the above description may be expressed by voltages, currents, electromagnetic waves, magnetic fields or particles, optical fields or particles, or predetermined (or selected) combinations thereof.

It may be appreciated by those skilled in the art that various logical blocks, modules, processors, means, circuits, and algorithm steps described in association with the embodiments disclosed herein may be implemented by electronic hardware, various types of programs or design codes (for easy description, herein, designated as software), or a combination of all of them. In order to clearly describe the intercompatibility of the hardware and the software, various components, blocks, modules, circuits, and steps have been generally described above in association with functions thereof. Whether the functions are implemented as the hardware or software depends on design restrictions given to a specific application and an entire system. Those skilled in the art of the present disclosure may implement functions described by various methods with respect to each specific application, but it should not be interpreted that the implementation determination departs from the scope of the present disclosure.

Various embodiments presented herein may be implemented as manufactured articles using a method, an apparatus, or a standard programming and/or engineering technique. The term manufactured article includes a computer program, a carrier, or a medium which is accessible by a predetermined (or selected) computer-readable storage device. For example, a computer-readable storage medium includes a magnetic storage device (for example, a hard disk, a floppy disk, a magnetic strip, or the like), an optical disk (for example, a CD, a DVD, or the like), a smart card, and a flash memory device (for example, an EEPROM, a card, a stick, a key drive, or the like), but is not limited thereto. Further, various storage media presented herein include one or more devices and/or other machine-readable media for storing information.

It will be appreciated that a specific order or a hierarchical structure of steps in the presented processes is one example of accesses. It will be appreciated that the specific order or the hierarchical structure of the steps in the processes within the scope of the present disclosure may be rearranged based on design priorities. Appended method claims provide elements of various steps in a sample order, but the method claims are not limited to the presented specific order or hierarchical structure.

The description of the presented embodiments is provided so that those skilled in the art of the present disclosure use or implement the present disclosure. Various modifications of the embodiments will be apparent to those skilled in the art and general principles defined herein can be applied to other embodiments without departing from the scope of the present disclosure. Therefore, the present disclosure is not limited to the embodiments presented herein, but should be interpreted within the widest range which is coherent with the principles and new features presented herein.

The various embodiments described above can be combined to provide further embodiments. All of the U.S. patents, U.S. patent application publications, U.S. patent applications, foreign patents, foreign patent applications and non-patent publications referred to in this specification and/ or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of analyzing a lesion based on a medical image performed by a computing device including at least one processor, the method comprising:
   extracting, by using a pre-trained artificial neural network, a first feature for each tile of a plurality of tiles included in an input image; and
   extracting, by using the pre-trained artificial neural network, a second feature for an entirety of the input image, based on both information about whether the lesion is present for the each tile and information on a pattern of the lesion for the each tile generated based on first features of the plurality of tiles.

2. The method of claim 1, wherein the input image is an image including a prostate tissue,
   the pattern of the lesion corresponds to a Gleason pattern, and the method further comprises determining, by using the pre-trained artificial neural network, a prostate cancer score for the entirety of the input image based on the second feature.

3. The method of claim 1, wherein the extracting the second feature for the entirety of the input image includes:
sampling some tiles of the plurality of tiles; and
extracting, by using the pre-trained artificial neural network, the second feature based on analysis data representing whether the lesion is present for the sampled tiles and analysis data representing the pattern of the lesion for the sampled tiles.

4. The method of claim 1, further comprising:
before the extracting the second feature for the entirety of the input image:
analyzing, by using the pre-trained artificial neural network and based on the first features of the plurality of tiles, whether the lesion is present for the each tile; and
analyzing, by using the pre-trained artificial neural network and based on the first features of the plurality of tiles, the pattern of the lesion for the each tile.

5. The method of claim 4, wherein the analyzing whether the lesion is present for the each tile and the analyzing the pattern of the lesion for the each tile are performed in an encoder part of the pre-trained artificial neural network, and the extracting the second feature for the entirety of the input image is performed in a decoder part of the pre-trained artificial neural network.

6. The method of claim 4, wherein the analyzing whether the lesion is present for the each tile includes:
determining, by using a main model of the pre-trained artificial neural network, a first probability value representing whether the lesion is present for the each tile of the plurality of tiles;
determining, by using a sub model of the pre-trained artificial neural network, a second probability value representing whether the lesion is present for the each tile of the plurality of tiles; and
correcting the first probability value based on the second probability value, and
wherein the sub model corresponds to a model trained based on tile-level labeling.

7. The method of claim 4, wherein the analyzing the pattern of the lesion for the each tile includes:
determining, by using a sub model of the pre-trained artificial neural network, a probability value representing whether the lesion is present for the each tile of the plurality of tiles; and
correcting the pattern of the lesion for the each tile based on the probability value,
wherein the sub model corresponds to a model trained based on tile-level labeling.

8. The method of claim 1, further comprising:
generating, based on the information on the pattern of the lesion for the each tile, a map representing the pattern of the lesion included in the input image as a first output;
determining, by using the pre-trained artificial neural network, an evaluation score of the lesion for the entirety of the input image based on the second feature; and
generating the determined evaluation score as a second output.

9. The method of claim 1, further comprising:
determining, by using the pre-trained artificial neural network, an evaluation score of the lesion for the input image based on the second feature,
wherein the pre-trained artificial neural network includes a main model trained based on a comparison between an evaluation score determined for a predetermined image and a score labeled to the predetermined image.

10. The method of claim 9, wherein the pre-trained artificial neural network includes the main model additionally trained without tile-level labeling based on a comparison between an average of first probability values representing whether the lesion is present in a plurality of tiles included in the predetermined image and a probability value labeled to the predetermined image.

11. The method of claim 9, wherein the pre-trained artificial neural network includes the main model additionally trained without tile-level labeling by comparing patterns of the lesion of tiles satisfying a predetermined reference between images having corresponding patterns of the lesion at an image level.

12. A computer program stored in a non-transitory computer readable storage medium encoded with a data structure for causing one or more processors to perform operations for analyzing a medical image, the operations comprising:
extracting, by using a pre-trained artificial neural network, a first feature for each tile of a plurality of tiles included in an input image; and
extracting, by using the pre-trained artificial neural network, a second feature for an entirety of the input image, based on both information about whether the lesion is present for the each tile and information on a pattern of the lesion for the each tile generated based on first features of the plurality of tiles.

* * * * *